United States Patent [19]

Holtkamp, Sr.

[11] Patent Number: Plant 7,662

[45] Date of Patent: Oct. 1, 1991

[54] AFRICAN VIOLET PLANT NAMED LITTLE FLUORITE

[76] Inventor: Reinhold Holtkamp, Sr., Blumenstrasse 28, D 4242 Rees-Haffen, Fed. Rep. of Germany

[21] Appl. No.: 551,736

[22] Filed: Jul. 12, 1990

[51] Int. Cl.[5] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner

[57] ABSTRACT

A new and distinct cultivar of African violet named Little Fluorite which is a sport of Little Saphire, disclosed in U.S. Plant Pat. No. 6,106. Little Fluorite is characterized by its miniature growth habit; single, lilac flowers, frequently with 1-2 additional small petals in the center; strong stems which curve toward the center to form a compact bouquet above the leaves; profuse and continuous flowering; dark green, spear-shaped leaves; flowering 10-11 weeks after planting of unrooted shoot, and by its long lasting and non-dropping flowers.

1 Drawing Sheet

The present invention comprises a new and distinct cultivar of African violet plant, botanically known as *Saintpaulia ionantha,* and hereinafter referred to by the cultivar name Little Fluorite.

The new cultivar was referred to during the breeding and selection process by the designation K 87/132 and is a sport of Little Saphire, disclosed in my U.S. Plant Pat. No. 6,106. The female, or seed parent of the parent cultivar Little Sapphire was a cultivar designated *Saintpaulia schumensis.* The male, or pollen parent was a cultivar designated Z 25/S Mini. Little Fluorite is similar in all essential respects to Little Saphire except for its lilac blossom color. Little Fluorite was discovered in a flowering block of the parent cultivar Little Saphire, and subsequently selected. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Little Fluorite has not been observed under all possible environmental conditions. The phenotype may vary significantly with variations in environment such as temperature, light intensity and day length. The following observations, measurements and values describe the new cultivar as grown in a 4 cm pot in Haffen, West Germany and Nashville, Tenn. under greenhouse conditions which closely approximate those generally used in commercial practice.

The following traits have been repeatedly observed and are determined to be basic characteristics of Little Fluorite, which in combination distinguish this African violet as a new and distinct cultivar.

(1) Little Fluorite is a miniature violet and will not grow taller than 6-8 cm.

(2) The lilac flowers are single, but often have 1-2 additional small petals in the center.

(3) Strong wirelike and upright flower stems curving toward the center.

(4) First flash of flowers form a tight bouquet above the leaves.

(5) Profuse flowering; under good growing conditions continuous blooming.

(6) Each plant carries 8-10 and more upright flower stems each of which carries 4-6 and more flowers.

(7) Long lasting, non-dropping flowers.

(8) Plant saleable 10 to 11 weeks after planting of unrooted shoot.

(9) Seed capsules push slightly through.

(10) Dark green, hairy leaves.

(11) Spear-shaped leaves are 1.5 to 2.5 cm in size.

(12) After maturity the flowers dry off and remain on the peduncle.

The accompanying color photographic drawing shows a typical specimen plant of the new cultivar grown in a 4 cm pot. The plant is pictured next to a pencil highlighting the miniature size of Little Fluorite. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 a.m. in Nashville, Tenn.

Botanical classification: *Saintpaulia ionantha,* Ramat., c.v. Little Fluorite.

Parentage: Sport of Little Saphire disclosed in U.S. Plant Pat. No. 6,106.

Propagation: The new cultivar holds its distinguishing characteristics through successive propagations by leaf cuttings.

Plant: From 5 cm to 7 cm tall when grown in pots, and approximately 7-10 cm in diameter when fully grown.

Leaves:

*General form.*—Spear-shaped.

*Diameter.*—15-20 mm wide and 20-25 mm long.

*Texture.*—Leatherlike.

*Aspect.*—Shiny, hairy.

*Veins.*—Upperside: visible; underside: well pronounced, shiny, light green, on young leaves purplish red.

*Color (upperside).*—Yellow-Green Group 147 A and somewhat darker.

*Color (underside).*—Greyed-Purple Group 186 B to C with touches of Greyed-Green Group 194 C.

*Petiole.*—Strong, purplish brown, hairy.

Flowers:

*Buds.*—Size: 4–5 mm just before opening. Shape: Bell-shaped. Color: Lilac.

*Sepals.*—Five (5). Color: Brownish green.

*Calyx.*—Shape: Funnel-shaped. Aspect: Spear-shaped, hairy.

*Peduncle.*—Character: Strong, wirelike, upright, hairy. Color: Brownish green.

*Individual flowers.*—Size: 20–24 mm. Shape: Single, violet-shaped, often with 1–2 additional small petals in the center. Color (upperside): Purple-Violet Group 82 D to C, center almost 82 B. Under cooler temperatures and more intensive lighting, the lilac color tends to intensify. Color (underside): Violet Group 87 D. Borne: Each flower stem carries 4–6 and more flowers on strong, upright peduncle that are free standing above the leaves, thereby forming a compact bouquet. Flowering habit: Flowers 10–11 weeks after planting an unrooted plantlet.

Reproductive organs:

*Stamens.*—Two (2). Anthers: 2 composed of 4 anther cells, seed capsule pushes slightly through.

*Filaments.*—Greenish white, 2 mm long.

*Styles.*—6–7 mm long, very light lilac, base of ovary light green and hairy.

Roots: Normally developed, white when young, turning slightly brownish when older.

Disease resistance: Good.

General observations: Little Fluorite is a super miniature violet, which does not grow taller than 6–8 cm. The single, lilac flowers often have 1–2 additional small petals in the center. The flowers are very long-lasting and non-dropping. Little Fluorite has continuous blooming characteristics, and under good growing conditions, it will not stop blooming. A nice bouquet of flowers free standing above the leaves develops approximately 10–11 weeks after planting an unrooted plantlet. Each of the 8–10 and more strong flower stems carries 4–6 and more flowers. The dark green leaves are spear-shaped.

I claim:

1. A new and distinct cultivar of African violet named Little Fluorite, as described and illustrated, and particularly characterized by its miniature growth habit; single, lilac flowers, frequently with 1–2 additional small petals in the center; strong stems which curve toward the center to form a compact bouquet above the leaves; profuse and continuous flowering; dark green, spear-shaped leaves; flowering 10–11 weeks after planting of unrooted shoot, and by its long lasting and non-dropping flowers.

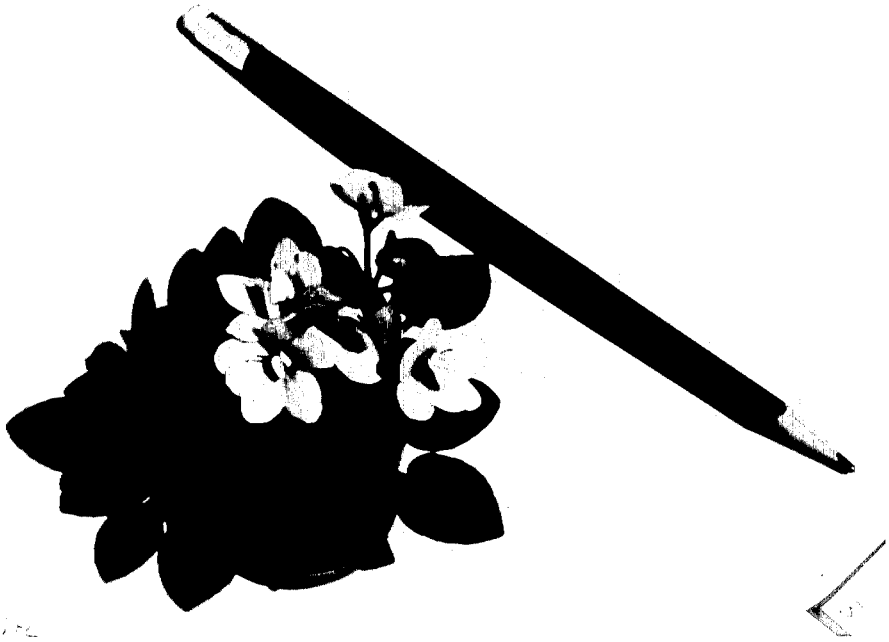

* * * * *